(12) United States Patent
Clarén et al.

(10) Patent No.: US 6,524,333 B1
(45) Date of Patent: Feb. 25, 2003

(54) DEVICE FOR THERAPEUTICAL TREATMENT OF A BLOOD VESSEL

(75) Inventors: Jan Clarén, Lund (SE); Stig Steen, Lund (SE)

(73) Assignee: Lars Sunnanvader, Hechingen (DK)

(*) Notice: Subject to any disclaimer, the term of this patent is extended or adjusted under 35 U.S.C. 154(b) by 0 days.

(21) Appl. No.: 09/582,676
(22) PCT Filed: Dec. 23, 1998
(86) PCT No.: PCT/SE98/02446
§ 371 (c)(1),
(2), (4) Date: Aug. 17, 2000
(87) PCT Pub. No.: WO99/35999
PCT Pub. Date: Jul. 22, 1999

(30) Foreign Application Priority Data

Dec. 30, 1997 (SE) .................................... 9704906

(51) Int. Cl.[7] ................................ A61F 2/06
(52) U.S. Cl. ................. 623/1.11; 623/1.15; 604/22
(58) Field of Search ............... 623/1.11, 1.15; 604/22

(56) References Cited

U.S. PATENT DOCUMENTS

| | | | | |
|---|---|---|---|---|
| 5,078,736 A | * | 1/1992 | Behl .......................... 623/1 |
| 5,722,979 A | * | 3/1998 | Kusleika .................... 606/108 |
| 5,776,184 A | * | 7/1998 | Tuch .......................... 623/1 |
| 5,779,643 A | * | 7/1998 | Lum et al. .................. 600/462 |
| 6,053,873 A | * | 4/2000 | Govari et al. ............... 600/505 |
| 6,361,554 B1 | * | 3/2002 | Brisken ....................... 623/1.1 |

FOREIGN PATENT DOCUMENTS

| | | |
|---|---|---|
| EP | 0 761 251 | 3/1997 |
| GB | 2 126 901 | 4/1984 |
| GB | 2 153 235 | 8/1985 |

OTHER PUBLICATIONS

International Search Report for application PCT/SE98/02446, dated Jun. 16, 1999.

* cited by examiner

Primary Examiner—John J. Calvert
Assistant Examiner—Katherine Moran
(74) Attorney, Agent, or Firm—Merchant & Gould, P.C.

(57) ABSTRACT

The invention relates to a device for therapeutical treatment of a blood vessel. It comprises in combination a stent, a balloon catheter for the insertion of the stent into a blood vessel, and a generator for generating ultrasound. The stent can be expanded radially and is of such construction that it is caused to vibrate and/or develop heat when exposed to ultrasound. Inserted into the blood vessel the stent can be expanded by means of the balloon catheter to engage the inside surface of the blood vessel in order to be left in the expanded condition as an inside lining in the blood vessel after the balloon catheter having been withdrawn from the blood vessel. Energy is transferred wirelessly by means of ultrasound generated by the generator, from an extracorporeal position to the stent as located in the blood vessel engaging the inside surface thereof.

11 Claims, 4 Drawing Sheets

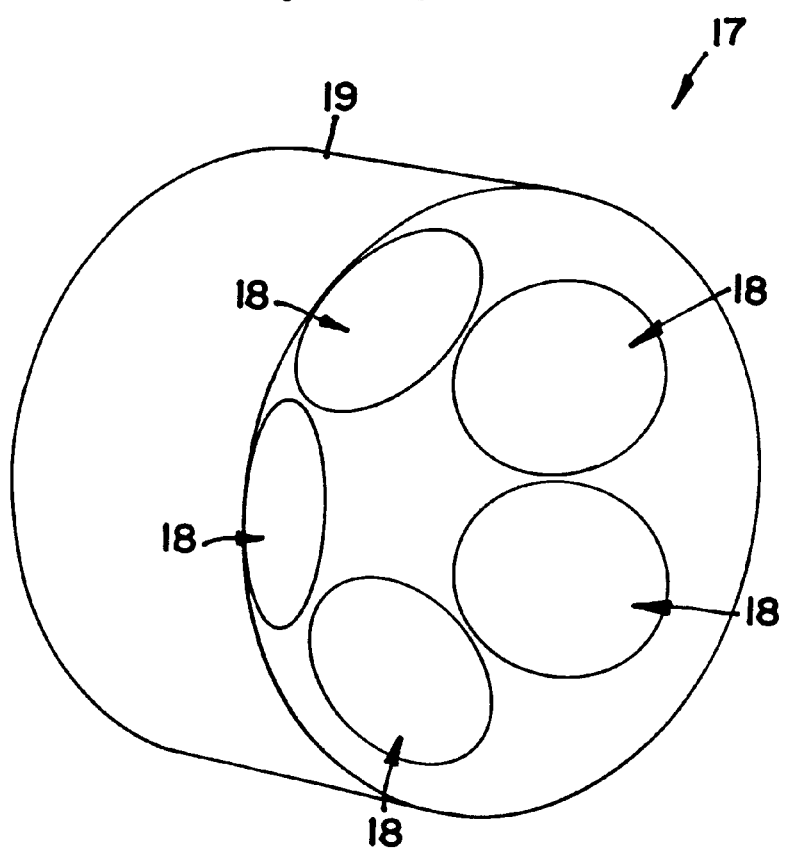

DEVICE FOR THERAPEUTICAL TREATMENT OF A BLOOD VESSEL

The invention relates to a device for therapeutical treatment of a blood vessel.

U.S. Pat. No. 5,078,736 describes a stent which can be introduced into a blood vessel by means of a balloon catheter and which can be expanded radially to engage the inside surface of the blood vessel in order that the stent after withdrawal of the balloon catheter from the blood vessel will be left in the expanded condition thereof as an inside lining in the blood vessel. The stent comprises an electrically conducting socket which can be heated when located in the blood vessel, by means of an extra-corporeally located power source in order to provide an intended therapeutic effect in the blood vessel.

In one embodiment this heating is effected inductively i.e. without wire connection between the stent and the power source. Since the stent has a small mass a powerful coil is, however, required for heating the stent to the necessary temperature inductively and it may even be necessary to allow the induction coil to operate at such a high power that water cooling thereof may be necessary, which makes the device expensive in manufacture and also cumbersome in use.

The purpose of the invention is to provide a much more easily handled device for wireless external influence on the stent, and for this purpose the invention provides a device of the kind referred to above with the features of claim 1.

The use of ultrasound for therapeutic purposes is known per se. E.g. GB-A-2 126 901 discloses an ultrasound hyperthermia applicator for heating relatively large tissue. volumes by ultrasound energy.

The invention also relates to a method for therapeutic treatment of a blood vessel comprising the steps of inserting a stent into the blood vessel by means of a balloon catheter, expanding the stent by means of the balloon catheter to engagement with the inside surface of the blood vessel, withdrawing the balloon catheter from the blood vessel, the expanded stent being left in the blood vessel in engagement with the inside surface thereof, and exposing the stent left in the blood vessel to an extra-corporeally generated ultrasound field in order to provide a therapeutical effect in the blood vessel in the region of the stent.

Figure 1:
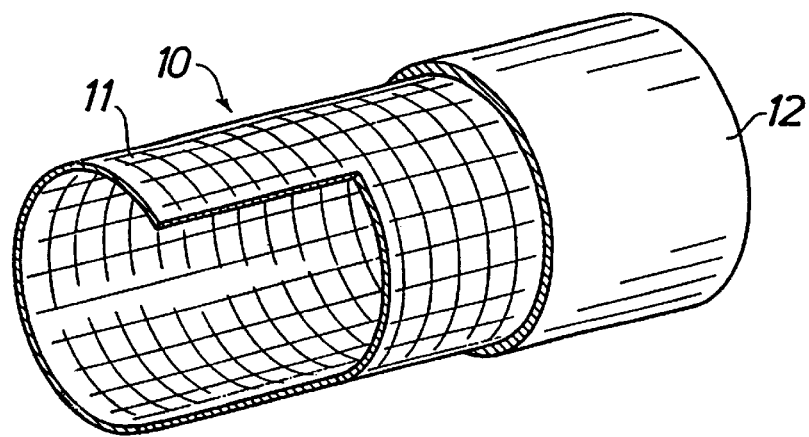
Figure 2:
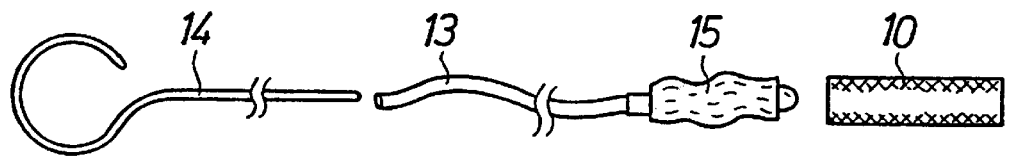
Figure 3:
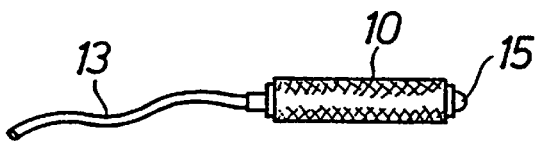
Figure 4:
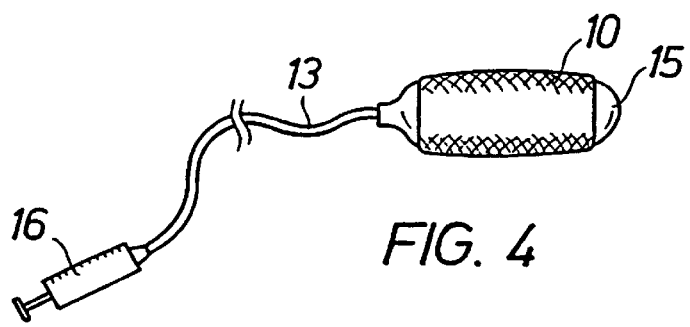
Figure 5:
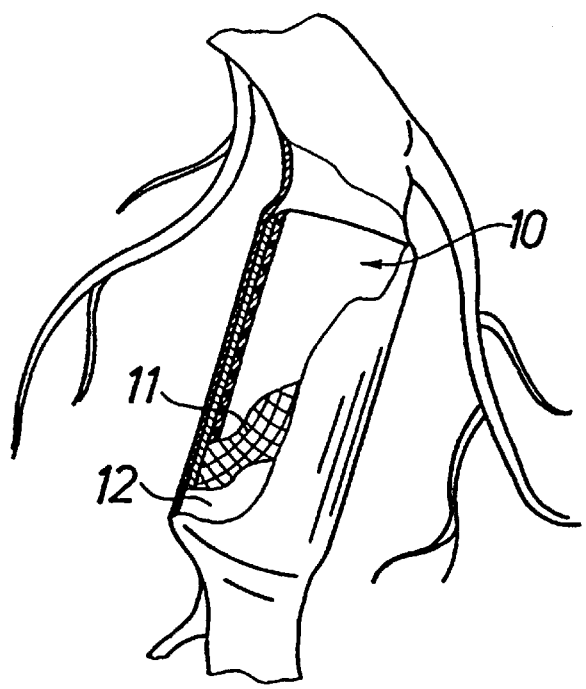
Figure 6:
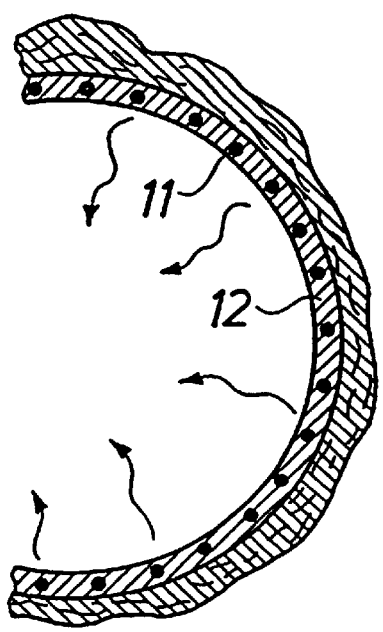
Figure 7:
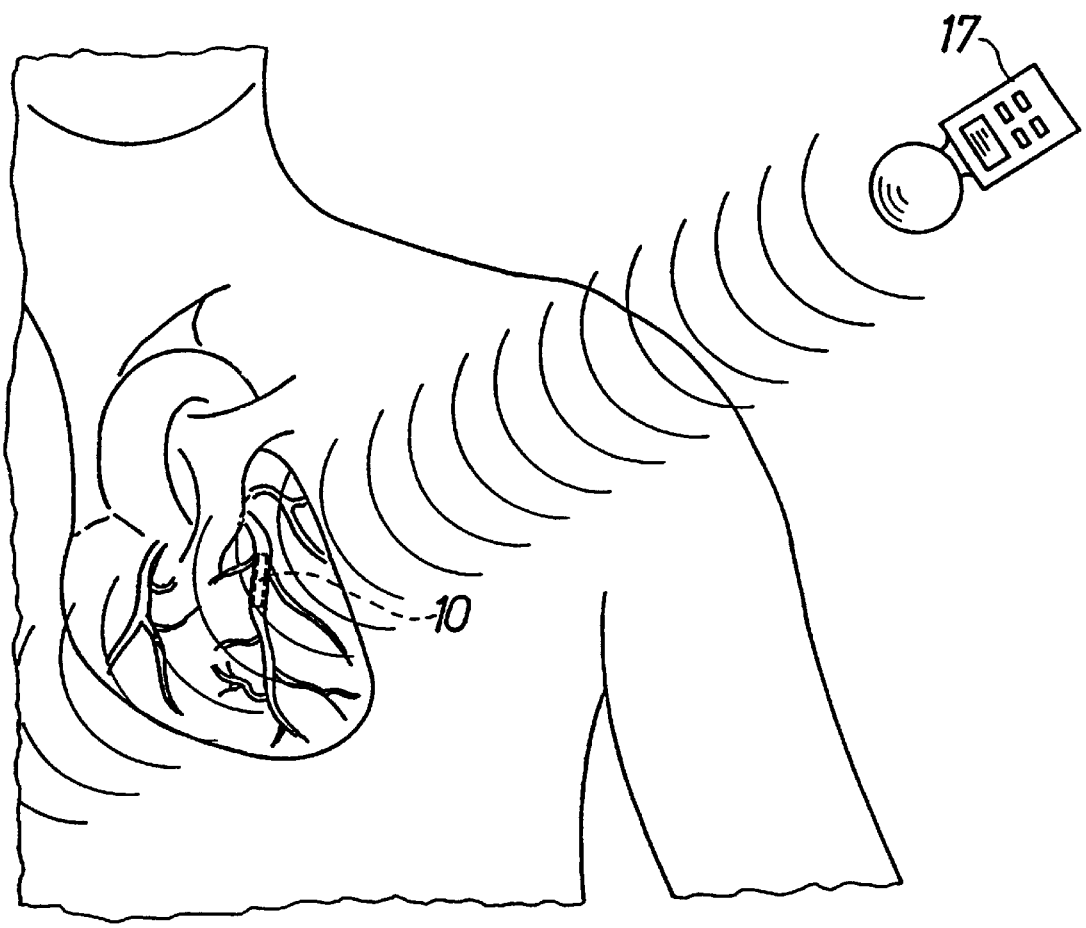

In order to explain the invention in more detail an embodiment thereof will be described below reference being made to the accompanying drawings in which FIG. 1 is a partly broken away perspective view of the stent forming part of the device according to the invention, FIG. 2 is a side view of a balloon catheter forming part of the device and having a guide wire, and the stent said elements being shown separated, FIG. 3 is a side view of the balloon catheter with the stent applied to the catheter for insertion into a blood vessel, FIG. 4 is a side view of the balloon catheter under expansion of the balloon and the stent applied on the balloon, FIG. 5 is a side view with portions broken away of the stent inserted into the blood vessel, FIG. 6 is an enlarged fragmentary cross-sectional view of the blood vessel and the stent inserted therein, and FIG. 7 is a fragmentary view of a human body with the stent inserted into a coronary vessel the stent being affected by an ultrasound field generated extra-corporeally by the generator forming part of the device.

FIG. 8 is a perspective view of an example ultrasound generator including multiple ultrasound transmitters mounted to a reflector.

The stent disclosed in FIG. 1 is indicated generally with 10 and comprises a socket 11 of such kind that it can be expanded radially. The socket can comprise a netting or an axially slotted socket, and it can be made of metal, e.g. stainless steel, or of plastic, e.g. a polymer. If the socket is made of plastic this can be cross-linked so that the plastic has a memory by which it assumes, at heating, a larger diameter than that it had before heating. The socket can have a length of the order of 0.5–10 cm, an inside diameter of the order of 1.0–15.0 mm, and a wall thickness of the order of a a tenth mm or two. The diameters have to be adjusted to the blood vessel wherein the stent is to be used. An expandable heat insulating cover 12 is provided on the outside of the socket 11, and this cover can consist of plastic, silicon rubber, graft, or the like. The stent can also be coated on the outside thereof and/or on the inside thereof with silicon rubber or graft, possibly with carbon powder (carbon black) mixed therewith.

For application of the stent a balloon catheter according to FIGS. 2–4 is used, which comprises a stem 13 having three lumen one receiving a guide wire 14 and the other two supplying and draining a liquid, e.g. a salt solution, to and from, respectively, a balloon 15 at one end of the stem. The liquid can be heated and can be supplied under pressure by means of a syringe 16 connected to the other end of the stem, FIG. 4. The stent 10 is located on the outside of the balloon when the balloon is collapsed, FIG. 3, and is inserted by means of the balloon catheter in a known manner into a blood vessel. When the stent is positioned at the intended site in the blood vessel the balloon is put under pressure by pumping liquid, possibly heated, into the balloon under radial expansion of the stent so that the cover 12 thereof will engage the inside surface of the blood vessel. The stent is of such kind that this expansion of the stent provides a permanent change of the shape of the stent so that the stent when the balloon is then collapsed by draining liquid therefrom and the balloon catheter thereafter is withdrawn from the blood vessel will remain in the blood vessel in the manner shown in FIGS. 5 and 6, engaging the inside surface of the wall of the blood vessel. The stent thus forms a lining in the blood vessel.

The stent is of such kind that it can function as target and receiver of energy generated extra-corporeally as ultrasound in order that the stent will be affected in some way for example in order to develop heat, to vibrate, to change size, to release a substance etc.

According to FIG. 7 the stent 10 is inserted into a coronary vessel and ultrasound energy is supplied to the stent from an extra-corporeally located ultrasound generator 17. The stent may not or should not be metallic in this case. It is most favourable if the stent is made of a material having an acoustic impedance which is the same as the impedance of the surrounding tissue (the wall of the vessel) the material of the stent at the same time providing a great attenuation of the ultrasound. All ultrasound from the generator 17 arriving at the stent will pass into the stent, and when the ultrasound is attenuated in the material of the stent the ultrasound energy will be converted into heat. There is also a possibility that the interface between the stent and the tissue will be heated if the acoustic impedance of the stent and the acoustic impedance of the tissue are slightly different. However, the heat conductivity of the stent in that case must differ from that of the tissue. The effect provided by the ultrasound is dependent of the frequency of the ultrasound, which also defines the depth in the body reached by the ultrasound; higher frequencies provide a shorter range in the body. It is also possible that the ultrasound consisting of small vibrations causes vibration of the stent at high frequency.

The ultrasound generator in a known manner, such as that shown in FIG. 8, can comprise a number of ultrasound transmitters 18 which are mounted to a spherically concave surface of a carrier or reflector 19 of plastic in order to focus the ultrasound beams emitted by the individual ultrasound transmitters to a common point. At the therapeutic treatment this point is located on the stent or a position in close juxtaposition of the stent.

The stent either the socket 10 with or without coating, or the cover 11, or both, can be of such nature that some therapeutically active substance is released from the stent at heating or vibration. It is also conceivable that the stent is of such nature that the radial dimension thereof will decrease or increase by heating of the stent.

The device according to the invention allows repeated therapeutic treatment of the blood vessel, which preferably is effected during the first six weeks after insertion of the stent. By heating of the stent or by imparting vibration to the stent when energy is supplied to the stent extra-corporeally it can be prevented that biologic material grows inside the stent, so called sub-intimal hyperplaci, and that cells already formed are removed. Due to the fact that the stent has a heat insulating cover 12 heat energy developed in the stent will be directed inwards (subintimally) into the stent as indicated by arrows in FIG. 6. Endotel cells will cover the stent and will be present between the blood and the stent. Without a heat insulating cover or if the cover functions as receiver of ultrasound energy the heat energy can also be directed outwards towards media in the blood vessel in order to retard the migration of smooth muscle cells from media to subendotelial position. Two or more stents can be provided mutually spaced in a blood vessel or a system of blood vessels so that the therapeutical effect will be provided between the stents along a distance of the blood vessel or the system of blood vessels, respectively.

The socket 11 can be coated with a composition for slow release of a pharmacon which prevents or retards the growth of coating (plaque) on the inside surface of the socket.

What is claimed is:

1. Device for therapeutic treatment of a blood vessel comprising a radially expandable stent a balloon catheter for insertion of the stent into the blood vessel and expansion thereof to engagement with an inside surface of the blood vessel in order that the stent will be left in the expanded condition thereof as an inside lining in the blood vessel after withdrawal of the balloon catheter from the blood vessel, and means for wireless transmission of energy from an extra-corporal position to the stent at the site thereof in the blood vessel, engaging the inside surface thereof, wherein said means comprises a generator for generating ultrasound energy and that the stent is of such nature that it is brought to vibrate and thereby to heat up when exposed to ultrasound.

2. Device according to claim 1, characterized in that the stent (11) has an acoustic impedance which is substantially in agreement with the acoustic impedance of body tissue.

3. Device according to claim 1, characterized in that the stent comprises a socket (11) formed as a netting, axially slotted, or shaped in another way in order to be radially expandable.

4. Device according to claim 3, characterized in that the socket (11) is metallic.

5. Device according to claim 3, characterized in that the socket (11) is provided with a radially expandable coating (12).

6. Device according to claim 5, characterized in that the coating (12) consists of silicon rubber or graft.

7. Device according to claim 6, characterized in that carbon powder is mixed with the coating (12).

8. Device according to claim 3, characterized in that the socket consists of plastic.

9. Device according to any of claims 1, characterized in that a therapeutic substance is contained by the stent said substance being releasable from the stent by heating or vibration thereof.

10. Device according to any of claims 1, characterized in that the stent is coated with a composition for slow release of a pharmacon.

11. Device according to any of claims 1, characterized in that the generator comprises several ultrasound transmitters mounted to a reflector for concentration of the effect transmitted therefrom to a collection point on the stent or in the vicinity thereof.

* * * * *